(12) United States Patent
Ferek-Petric et al.

(10) Patent No.: US 8,002,700 B2
(45) Date of Patent: Aug. 23, 2011

(54) COMMUNICATIONS SYSTEM FOR AN IMPLANTABLE MEDICAL DEVICE AND A DELIVERY DEVICE

(75) Inventors: Bozidar Ferek-Petric, Zagreb (HR); Dwight H. Warkentin, Arden Hills, MN (US)

(73) Assignee: Medtronic, Inc., Minneapolis, MN (US)

( * ) Notice: Subject to any disclaimer, the term of this patent is extended or adjusted under 35 U.S.C. 154(b) by 1715 days.

(21) Appl. No.: 10/631,953

(22) Filed: Jul. 31, 2003

(65) Prior Publication Data

US 2004/0077995 A1    Apr. 22, 2004

Related U.S. Application Data

(63) Continuation-in-part of application No. 10/123,958, filed on Apr. 17, 2002, now Pat. No. 6,824,512, which is a continuation of application No. 09/475,709, filed on Dec. 30, 1999, now Pat. No. 6,471,645.

(51) Int. Cl.
*A61B 5/00* (2006.01)

(52) U.S. Cl. .................. 600/300; 607/3; 607/9; 607/17; 607/18; 607/32; 600/301

(58) Field of Classification Search .................. 600/300, 600/301; 128/903–905, 920
See application file for complete search history.

(56) References Cited

U.S. PATENT DOCUMENTS

| | | | |
|---|---|---|---|
| 4,146,029 A * | 3/1979 | Ellinwood, Jr. ............ 604/891.1 |
| 4,360,125 A | 11/1982 | Martindale et al. ................ 221/2 |
| 4,494,950 A | 1/1985 | Fischell ........................... 605/66 |
| 4,768,176 A | 8/1988 | Kehr et al. ....................... 368/10 |
| 4,768,177 A | 8/1988 | Kehr et al. ....................... 368/10 |
| 4,987,897 A | 1/1991 | Funke ...................... 128/419 PG |
| 5,113,869 A * | 5/1992 | Nappholz et al. ............. 600/508 |
| 5,200,891 A | 4/1993 | Kehr et al. ............... 365/413.01 |
| 5,609,612 A * | 3/1997 | Plicchi et al. ................... 607/17 |
| 5,642,731 A | 7/1997 | Kehr ............................. 128/630 |
| 5,752,235 A | 5/1998 | Kehr et al. ......................... 705/3 |
| 5,752,976 A | 5/1998 | Duffin et al. .................... 607/32 |
| 5,954,641 A | 9/1999 | Kehr et al. ..................... 600/300 |
| 5,971,594 A | 10/1999 | Sahai et al. ............... 364/479.12 |

(Continued)

FOREIGN PATENT DOCUMENTS

EP    0 526 166 A2    2/1993

(Continued)

OTHER PUBLICATIONS

Advantor Corporation Products; Product Sheet; http://www.advantor.com/products.html; Oct. 21, 1999.
InforMedix, Inc.; MediMonitor Product Sheet; http://www.informedix.com/print-site.html; Oct. 21, 1999.

*Primary Examiner* — Sam Yao
*Assistant Examiner* — Kai Rajan (57) ABSTRACT

A closed loop system for monitoring drug dose, intake and effectiveness includes a drug delivery device in data communications with at least one implantable medical device. The system is preferably implemented in a web-enabled environment in which a remote data center communicates with the implantable devices (IMDs) in a patient via a programmer or the pill dispenser. A physician, clinician, or other user may access the remote data center to review and monitor the IMDs or the drug delivery regime remotely. The system further provides a dynamic drug management system, compatible with a web-enabled interactive data communication environment that accurately monitors dose and specific drug effectiveness in a patient to enhance patient care.

22 Claims, 6 Drawing Sheets

U.S. PATENT DOCUMENTS

| | | |
|---|---|---|
| 6,361,522 B1 * | 3/2002 | Scheiner et al. ............... 604/67 |
| 6,386,882 B1 | 5/2002 | Linberg ....................... 434/262 |
| 6,443,891 B1 | 9/2002 | Grevious ...................... 600/302 |
| 6,471,645 B1 | 10/2002 | Warkentin et al. ............. 600/300 |
| 6,553,262 B1 | 4/2003 | Lang et al. .................... 607/32 |
| 2002/0111542 A1 | 8/2002 | Warkentin et al. ............. 600/300 |
| 2003/0130616 A1 * | 7/2003 | Steil et al. ..................... 604/66 |

FOREIGN PATENT DOCUMENTS

| | | |
|---|---|---|
| EP | 1 022 035 A1 | 7/2000 |
| WO | WO 01/48676 A1 | 5/2001 |

* cited by examiner

COMMUNICATIONS SYSTEM FOR AN IMPLANTABLE MEDICAL DEVICE AND A DELIVERY DEVICE

CROSS REFERENCE TO RELATED APPLICATIONS

The present application is a continuation-in-part of Ser. No. 10/123,958, filed on Apr. 17, 2002 now U.S. Pat. No. 6,824,512, which is a continuation of a 09/475,709, filed on Dec. 30, 1999 now U.S. Pat. No. 6,471,645. Both of which are herein incorporated by reference in their entirety.

THE FIELD OF THE INVENTION

The present invention relates to implantable medical devices (IMDs). More specifically, the present invention relates to communication between IMD's and external devices.

BACKGROUND OF THE INVENTION

A technology-based health care system that fully integrates the technical and social aspects of patient care and therapy should be able to connect the client with care providers irrespective of separation distance or location of the participants. Currently, clinical services are generally limited to in-hospital operations. For example, if a physician needs to review the performance parameters of an implantable device in a patient, it is likely that the patient has to go to the clinic. Further, if the medical conditions of a patient with an implantable device warrant a continuous monitoring or adjustment of the device, the patient would have to stay in a hospital indefinitely. Further, if the patient with the IMDs is taking a drug, it is often clinically prudent to monitor the dose and its impact on the patient and, as well, on the IMDs. Such a continued treatment plan poses both economic and social problems. Under the exemplary scenario, as the segment of the population with implanted medical devices increases many more hospitals/clinics including service personnel will be needed to provide in-hospital service for the patients, thus escalating the cost of healthcare. Additionally the patients will be unduly restricted and inconvenienced by the need to either stay in the hospital or make very frequent visits to a clinic.

Often, a patient will visit a clinic center for retrieval of data from the implanted device to assess the operations of the device and gather patient history for both clinical and research purposes. Such data is acquired by having the patient in a hospital/clinic to download the stored data from the implantable medical device. Depending on the frequency of data collection this procedure may pose serious difficulty and inconvenience for patients who live in rural areas or have limited mobility. Similarly, in the event a need arises to upgrade the software of an implantable medical device, the patient will be required to come into the clinic or hospital to have the upgrade installed.

Advances in modern patient therapy and treatment have made it possible to implant a number of devices in a patient; however, managing and integrating these various devices is difficult. For example, IMDs such as a defibrillator or a pacemaker, a neural implant, a drug pump, a separate physiologic monitor and various other IMDs may be implanted in a single patient. To successfully manage the operations and assess the performance of each device in a patient with multi-implants requires a continuous update and monitoring of the devices. As is often the case, patients with multi-implanted medical devices may take a variety of medications. It is therefore necessary to monitor drug intake and its effect on the operational and functional parameters of the IMDs. Additionally, chronic monitoring of drug intake and its effect on the physiological and clinical conditions of the patient enables a pro-active intervention to change the course of an otherwise serious medical condition. Thus, there is a need to monitor drug delivery and effectiveness in conjunction with IMD performance.h

SUMMARY OF THE INVENTION

The present invention generally relates to a communications scheme in which an IMD is in communication with a drug delivery device. In several embodiments, the drug delivery device is, for example, a drug dispenser such as a pill box, drug delivering patch, inhaler, intravenous delivery mechanism, drug pump, or a transcutaneous or subcutaneous delivery mechanism. Communication between the IMD and the delivery device facilitates the delivery of the appropriate therapy, For example, upon detection of certain cardiac conditions the IMD could communicate with the delivery device to indicate that a particular drug should be administered in a particular dose. Similarly, the IMD indicates that a particular drug should be discontinued or that the dosage should be modified. Further, the delivery device can communicate with the IMD. For example, whenever a dose is to be delivered, the IMD is alerted. Thus,. the therapy delivered by the IMD could be tailored according the drug delivery. If an expected drug delivery is missed, the IMD self adjusts to accommodate the expected change.

In some embodiments, the delivery device is in data communication with a communications device. The communications device may facilitate communication with the IMD if the delivery device so requires an intermediary. In addition, the communications device acts as an interface for the delivery device and the IMD to communicate with a remote user. For example, the remote user may be a pharmacy or a health care provider. As the IMD detects changes that require an adjustment to a prescription, this information is communicated to the pharmacy or the health care provider. As dosages are taken, the communication could also simply alert the pharmacy that the prescription should be refilled, thus providing convenience to the patient and enabling a continuous medical care.

In another embodiment, a remote web-based expert data center interacts with a patient having one or more implantable medical devices (IMDs) via an associated external medical device, preferably a programmer, located in close proximity to the IMDs. The IMDs are adapted to communicate with a pill dispenser to monitor and log pill deposition and effectiveness. Various communications media interlink the remote web-based expert data center and the programmer to remotely exchange clinically significant information and ultimately effect real-time drug intake and prescriptive changes as needed.

In another embodiment, the present invention includes real-time access of a programmer or a pill dispenser to a remote web-based expert data center, via a communication network, which includes the Internet. The operative structure of the invention includes the remote web-based expert data center, in which an expert system is maintained, having a bi-directional real-time data, sound and video communications with the programmer via a broad range of communication link systems. The programmer is in turn in telemetric communications with the IMDs such that the IMDs may uplink to the programmer or the programmer may down link to the IMDs, as needed.

In another embodiment, the invention provides a system and method to remotely monitor drug effectiveness in a patient. Further, the invention enables a chronic evaluation of drugs in a patient on real time basis. The data collected in this manner could be used to influence the course of drug therapy.

BRIEF DESCRIPTION OF THE DRAWINGS

The present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DESCRIPTION OF THE PREFERRED EMBODIMENTS

Figure 1:
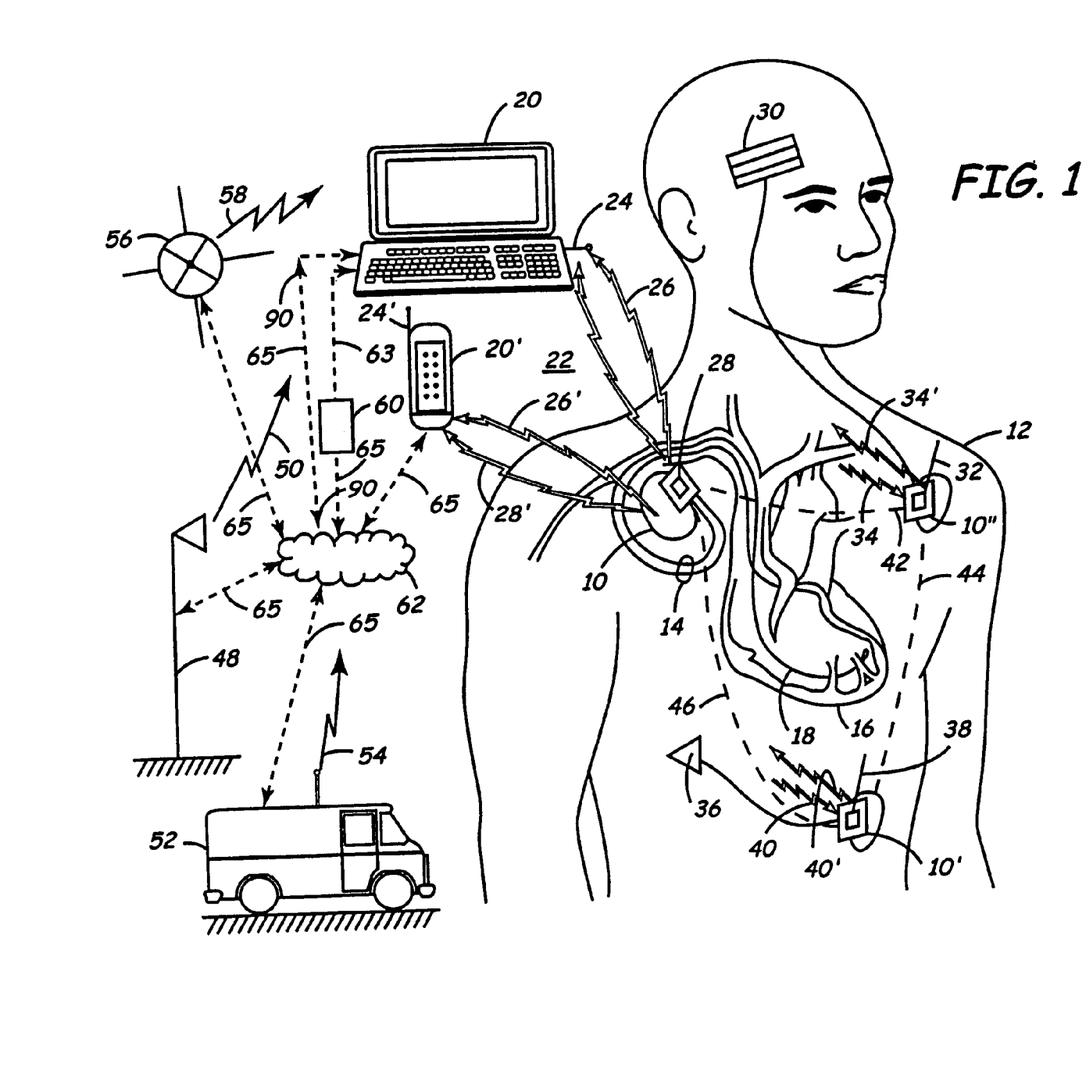
FIG. 1 is a simplified schematic diagram of major uplink and downlink telemetry communications between a remote clinical station, a programmer and a plurality of implantable medical devices (IMDs)

FIG. 1 is a simplified schematic of the major components of the present invention. Specifically, a bi-directional wireless communications system between programmer 20, pill dispenser 20' and a number of implantable medical devices (IMDs) represented by IMD 10, IMD 10' and IMD 10" is shown. The IMDs are implanted in patient 12 beneath the skin or muscle. The IMDs are electrically coupled to electrodes 18, 3 0, and 3 6 respectively in a manner known in the art. IMD 10 contains a microprocessor for timing, sensing and pacing functions consistent with preset programmed functions. Similarly, IMDs 10' and 10" are microprocessor-based to provide timing and sensing functions to execute the clinical functions for which they are employed. For example, IMD 10' could provide neural stimulation to the brain via electrode 30 and IMD 10" may function as a drug delivery system that is controlled by electrode 36. The various functions of the IMDs are coordinated using wireless telemetry. Wireless links 42, 44 and 46 jointly and severally couple IMDs 10, 10' and 10" such that programmer 20 may transmit commands or data to any or all the of IMDs via one of telemetry antennas 28, 32 and 38. This structure provides a highly flexible and economical wireless communications system between the IMDS. Further, the structure provides a redundant communications system, which enables access to any one of a multiplicity of IMDs in the event of a malfunction of one or two of antennas 28, 32 and 38.

Programming commands or data are transmitted from programmer 20 to IMDs 10, 10' and 10" via external RF telemetry antenna 24. Telemetry antenna 24 may be an RF head or equivalent. Antenna 24 may be located on programmer 20 externally on the case or housing. Telemetry antenna 24 is generally telescoping and may be adjustable on the case of programmer 20. Both programmer 20 and pill dispenser 20' may be placed within a few feet or further away from patient 12 and would still be within range to wirelessly communicate with telemetry antennas 28, 32 and 38.

The uplink to remote web-based expert data center 62, hereinafter referred to as, interchangeably, "data center 62", "expert data center 62" or "web-based data center 62" without limitations, is accomplished through programmer 20 or webtop unit 20'. Accordingly programmer 20 and webtop unit 20' function as an interface between IMDs 10, 10' and 10" and data center 62. One of the many distinguishing elements of the present invention includes the use of various scalable, reliable and high-speed wireless communication systems to bi-directionally transmit high fidelity digital/analog data between programmer 20 and data center 62.

There are a variety of wireless mediums through which data communications could be established between programmer 20 or pill dispenser 20' and data center 62. The communications link between Programmer 20 or pill dispenser 20' and data center 62 could be modem 60, which is connected to programmer 20 on one side at line 63 and data center 62 at line 64 on the other side. In this case, data is transferred from data center 62 to programmer 20 via modem 60. Alternate data transmission systems include, without limitations, stationary microwave and/or RF antennas 48 being wirelessly connected to programmer 20 via tunable frequency wave delineated by line 50. Antenna 48 is in communications with data center 62 via wireless link 65. Similarly, pill dispenser 20', mobile vehicle 52 and satellite 56 are in communications with data center 62 via wireless link 65. Further, mobile system 52 and satellite 56 are in wireless communications with programmer 20 or pill dispenser 20' via tunable frequency waves 54 and 58, respectively.

In one embodiment, a Telnet system is used to wirelessly access data center 62. Telnet emulates a client/server model and requires that the client run a dedicated software to access data center 62. The Telnet scheme envisioned for use with the present invention includes various operating systems including UNIX, Macintosh, and all versions of Windows.

Functionally, an operator at programmer 20 or an operator at data center 62 would initiate remote contact. Programmer 20 is down linkable to IMDs via link antennas 28, 32 and 38 to enable data reception and transmission. For example, an operator or a clinician at data center 62 may downlink to programmer 20 to perform a routine or a scheduled evaluation of programmer 20. In this case, the wireless communication is made via wireless link 65. If a downlink is required from programmer 20 to IMD 10 for example, the downlink is affected using telemetry antenna 22. In the alternate, if an uplink is initiated from patient 12 to programmer 20 the uplink is executed via wireless link 26. As discussed herein below, each antenna from the IMDs 10 can be used to uplink all or one of the IMDs to programmer 20. For example, IMD 10" which relates to neural implant 30 can be implemented to up-link, via wireless antenna 34 or wireless antenna 34', any one, two or more IMDs to programmer 20. Preferably BLUETOOTH chips, adopted to function within the body to outside the body and also adopted to provide low current drain, are embedded in order to provide wireless and seamless connections 42, 44 and 46 between IMDs 10, 10' and 10". The communication scheme is designed to be broadband compatible and capable of simultaneously supporting multiple information sets and architecture, transmitting at relatively high speed, to provide data, sound and video services on demand.

Figure 2:
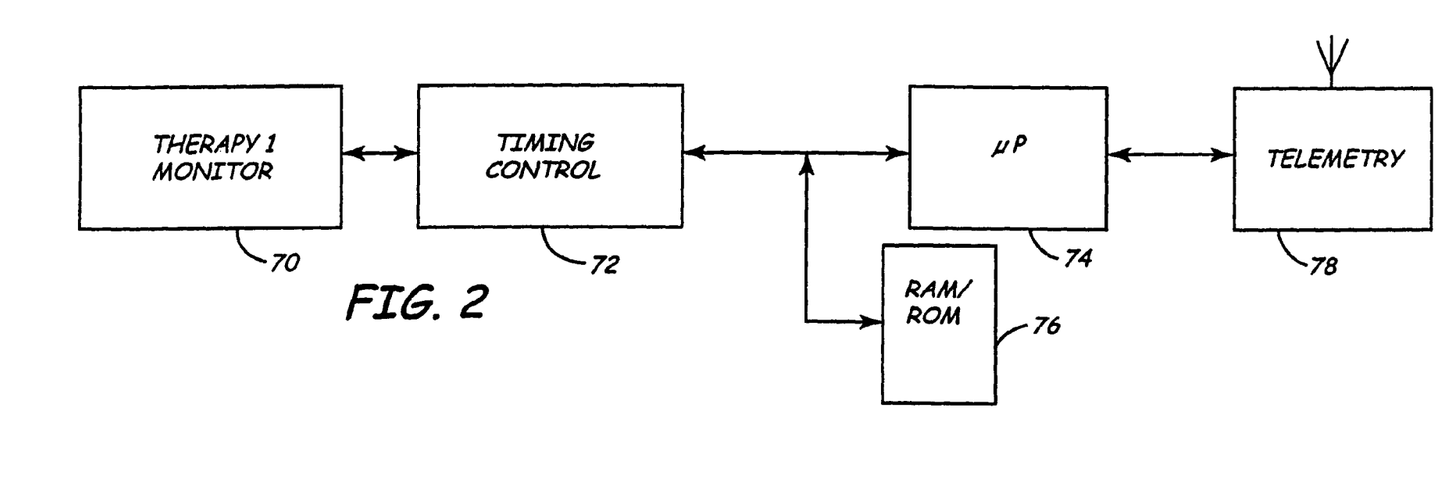
FIG. 2 is a block diagram representing the major components of an IMD.

FIG. 2 illustrates typical components of an IMD, such as those contemplated by the present invention. Specifically, major operative structures common to typical IMDs 10, 10' and 10" are represented in a generic format. In the interest of brevity, IMD 10 relative to FIG. 2 refers to all the other illustrated IMDs. Accordingly, IMD 10 is implanted in patient 12 beneath the patient's skin or muscle and is electrically coupled to heart 16 of patient 12 through pace/sense electrodes and lead conductor(s) of at least one cardiac pacing lead 18 in a manner known in the art. IMD 10 contains timing control 72 including operating system that may employ microprocessor 74 or a digital state machine for timing, sensing and pacing functions in accordance with a programmed operating mode. IMD 10 also contains sense amplifiers for detecting cardiac signals, patient activity sensors or other physiologic sensors for sensing the need for cardiac output, and pulse generating output circuits for delivering pacing pulses to at least one heart chamber of heart 16 under control of the operating system in a manner well known in the prior art. The operating system includes memory registers or RAM/ROM 76 for storing a variety of programmed-in operating mode and parameter values that are used by the operating system. The memory registers or RAM/ROM 76 may also be used for storing data compiled from sensed cardiac activity and/or relating to device operating history or sensed physiologic parameters for telemetry out on receipt of a retrieval or interrogation instruction. All of these functions and operations are well known in the art, and many are generally employed to store operating commands and data for controlling device operation and for later retrieval to diagnose device function or patient condition.

Programming commands or data are transmitted between IMD RF telemetry antenna 28, for example, and an external RF telemetry antenna 24 associated with programmer 20. In this case, it is not necessary that the external RF telemetry antenna 24 be contained in a programmer RF head so that it can be located close to the patient's skin overlying IMD 10. Instead, the external RF telemetry antenna 24 can be located on the case of programmer 20. It should be noted that programmer 20 can be located some distance away from patient 12 and is locally placed proximate to the IMDs such that the communication between IMDs 10, 10' and 10" and programmer 20 is telemetric. For example, programmer 20 and external RF telemetry antenna 24 may be on a stand a few meters or so away from patient 12. Moreover, patient 12 may be active and could be exercising on a treadmill or the like during an uplink telemetry interrogation of real-time ECG or other physiologic parameters. Programmer 20 may also be designed to universally program existing IMDs that employ RF telemetry antennas of the prior art and therefore also have a conventional programmer RF head and associated software for selective use therewith.

In an uplink communication between IMD 10 and programmer 20, for example, telemetry transmission 22 is activated to operate as a transmitter and external RF telemetry antenna 24 operates as a telemetry receiver. In this manner data and information may be transmitted from IMD10 to programmer 20. In the alternate, IMD 10 RF telemetry antenna 26 operates as a telemetry receiver antenna to downlink data and information from programmer 20. Both RF telemetry antennas 22 and 26 are coupled to a transceiver comprising a transmitter and a receiver.

Figure 3A:
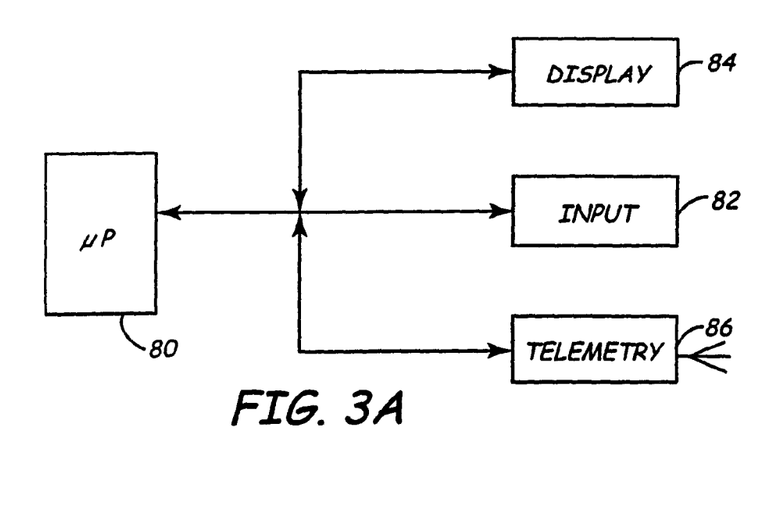
FIG. 3A is a block diagram presenting the major components of a programmer.

FIG. 3A is a simplified circuit block diagram of major functional components of programmer 20. The external RF telemetry antenna 24 on programmer 20 is coupled to a telemetry transceiver 86 and antenna driver circuit board including a telemetry transmitter and telemetry receiver 34. The telemetry transmitter and telemetry receiver are coupled to control circuitry and registers operated under the control of microcomputer 80. Similarly, within IMD 10, for example, the RF telemetry antenna 26 is coupled to a telemetry transceiver comprising a telemetry transmitter and telemetry receiver. The telemetry transmitter and telemetry receiver in IMD 10 are coupled to control circuitry and registers operated under the control of microcomputer 74.

Further referring to FIG. 3A, programmer 20 is a personal computer type, microprocessor-based device incorporating a central processing unit, which may be, for example, an Intel Pentium microprocessor or the like. A system bus interconnects CPU 80 with a hard disk drive, storing operational programs and data, and with a graphics circuit and an interface controller module. A floppy disk drive or a CD ROM drive is also coupled to the bus and is accessible via a disk insertion slot within the housing of programmer 20. Programmer 20 further comprises an interface module, which includes a digital circuit, a non-isolated analog circuit, and an isolated analog circuit. The digital circuit enables the interface module to communicate with interface controller module. Operation of the programmer in accordance with the present invention is controlled by microprocessor 80.

In order for the physician or other caregiver or operator to communicate with the programmer 20, a keyboard or input 82 coupled to CPU 80 is optionally provided. However the primary communications mode may be through graphics display screen of the well-known "touch sensitive" type controlled by a graphics circuit. A user of programmer 20 may interact therewith through the use of a stylus, also coupled to a graphics circuit, which is used to point to various locations on screen or display 84 which display menu choices for selection by the user or an alphanumeric keyboard for entering text or numbers and other symbols. Various touch-screen assemblies are known and commercially available. Display 84 and or the keyboard comprise means for entering command signals from the operator to initiate transmissions of downlink or uplink telemetry and to initiate and control telemetry sessions once a telemetry link with data center 62 or an implanted device has been established. Display screen 84 is also used to display patient related data and menu choices and data entry fields used in entering the data in accordance with the present invention as described below. Display screen 84 also displays a variety of screens of telemetered out data or real-time data. Display screen 84 may also display linked event signals as they are received and thereby serve as a means for enabling the operator to timely review link-history and status.

Programmer 20 further comprises an interface module, which includes digital circuit, non-isolated analog circuit, and isolated analog circuit. The digital circuit enables the interface module to communicate with the interface controller module. As indicated hereinabove, the operation of programmer 20, in accordance with the present invention, is controlled by microprocessor 80. Programmer 20 is preferably of the type that is disclosed in U.S. Pat. No. 5,345,362 to Winkler, which is incorporated by reference herein in its entirety.

Screen 84 may also display up-linked event signals when received and thereby serve as a means for enabling the operator of programmer 20 to correlate the receipt of uplink telemetry from an implanted device with the application of a response-provoking action to the patient's body as needed. Programmer 20 is also provided with a strip chart printer or the like coupled to interface controller module so that a hard copy of a patient's ECG, EGM, marker channel of graphics displayed on the display screen can be generated.

As will be appreciated by those of ordinary skill in the art, it is often desirable to provide a means for programmer 20 to adapt its mode of operation depending upon the type or generation of implanted medical device to be programmed and to be compliant with the wireless communications system through which data and information is transmitted between programmer 20 and data center 62.

Figure 3B:
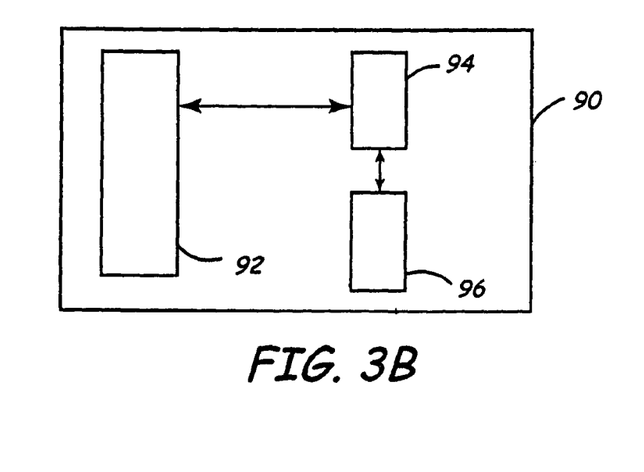
FIG. 3B is a block diagram representing a laser transceiver for high speed transmission of voice, video and other data.

FIG. 3B is an illustration of the major components of Wave unit 90 utilizing laser technologies such as for example the WaveStar Optic Air Unit, manufactured by Lucent Technologies or equivalent. This embodiment may be implemented for large data transfer at high speed in applications involving several programmers. The unit includes laser 92, transceiver 94 and amplifier 96. A first wave unit 90 is installed at data center 62 and a second unit 90' is located proximate to programmer 20 or pill dispenser 20'. Data transmission between remote data center 62 and programmer unit 20 is executed via wave units 90. Typically, the first wave unit 90 accepts data and splits it into unique wavelength for transmission. The second wave unit 90' recomposes the data back to its original form.

Figure 4A:
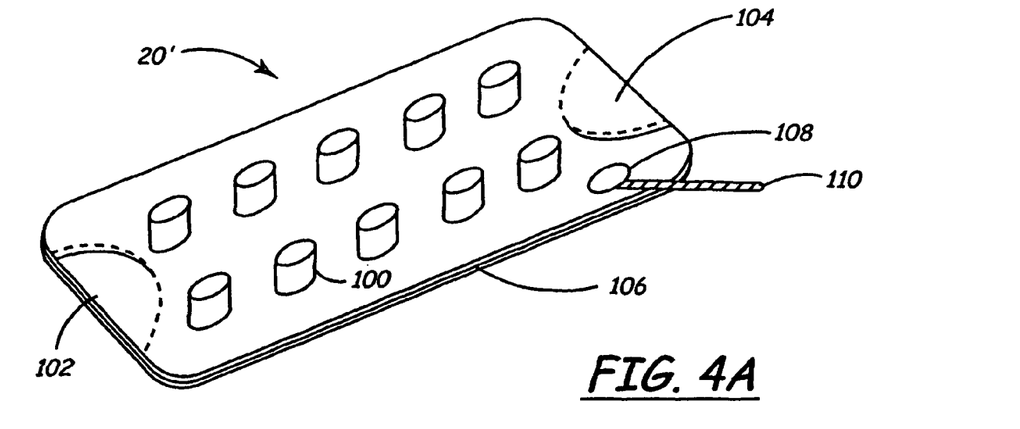
FIGS. 4A, 4B and 4C illustrate a perspective view, a side view and a schematic for the drug dispensing unit or interface medical unit, respectively.
Figure 4B:
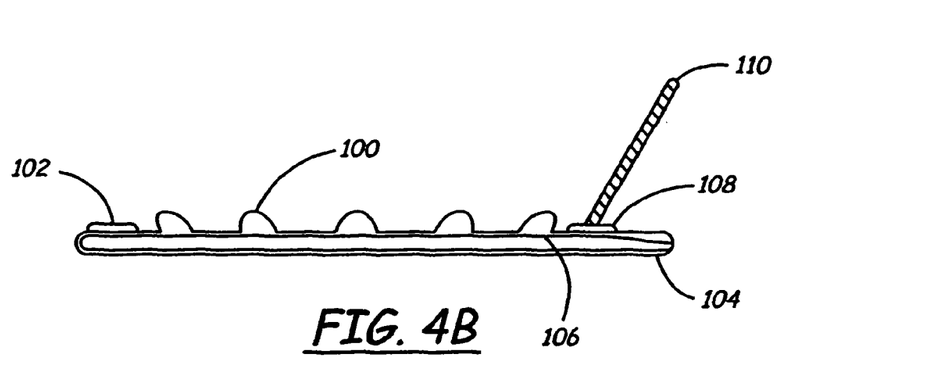
Figure 4C:
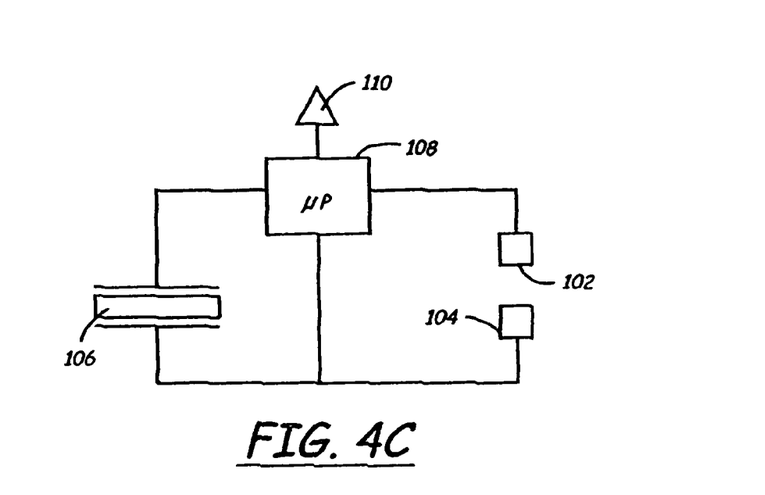

FIGS. 4A, 4B and 4C represent various views of pill dispenser unit 20'. The structure includes pill containers 100 that protrude upwards from the surface for pill or drug containment. The structure also includes upper metalized layer 102, superimposed on a plastic cover and lower metalized layer 104 superimposed on a plastic cover. Piezoelectric film 106 is disposed between the upper and the lower metalized layers. Further, microprocessor 108 is embedded between the upper and the lower layers. Telemetric antenna 110 is in electronic communications with microprocessor 108 and extends outward proximate therefrom.

Pill container 100 includes an indicator for the absence or presence of a pill in containers 100. Pill dispenser unit 20' is in preferably telemetric or equivalent wireless communications with IMDs 10, 10' and 10". In the alternate, pill dispenser unit 20' is in data communications with programmer 20.

Figure 5:
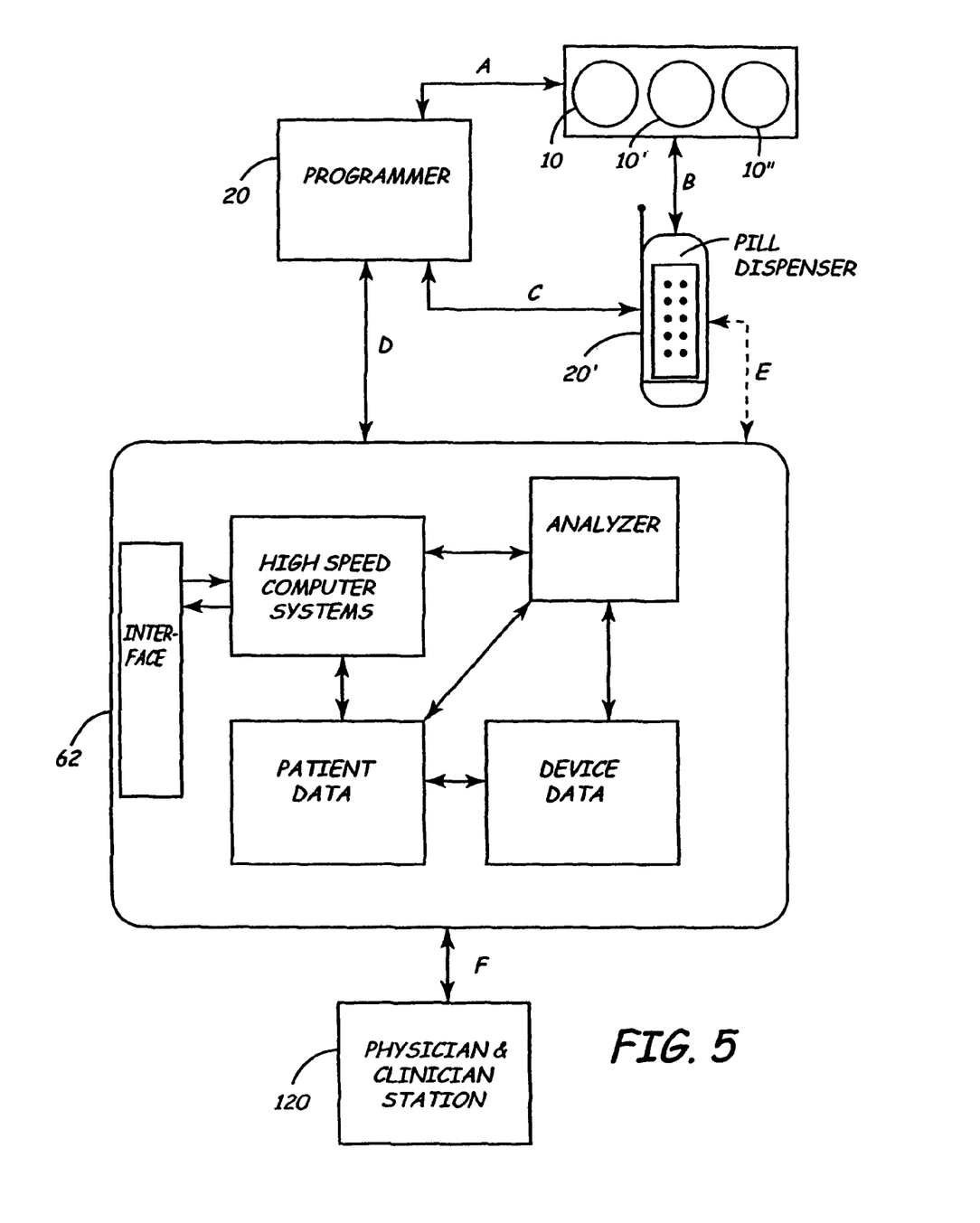
FIG. 5 is a block diagram representing the major data centers and the communication scheme according to the present invention.

Referring to FIG. 5, a communication scheme between remote data center 62, physician station 120 and programmer 20 and/or pill dispenser unit 20'. As indicated hereinabove, data center 62 includes high-speed computers and is preferably web enabled to provide remote access. Communication links A, B, C, D, E and F are preferably wireless although any other communication system such as cable, fiber-optics or equivalent could be implemented.

Generally, the present invention provides drug delivery and management primarily based on the chronic communications between pill dispenser unit 20' and IMDs 10, 10' and 10". Specifically, IMDs 10, 10' and 10" include a software program which would monitor the number of pills in pill dispenser 20' via link B which is equivalent to telemetry 110. In the alternate, the number of pills in dispenser 20' may be tracked via link C which establishes the communication between pill dispenser 20' and programmer 20. Pill dispenser 20' includes means for indicating the pill deposition from the package or container. Further IMDs 10, 10' and 10" include means for monitoring the deposition of the pills. A prescribed therapy schedule is preferably preprogrammed in the memory of IMDs 10, 10' and 10". The actual pill deposition in container 100 is known and correlates to one or more of the parameters programmed in IMDs 10, 10' and 10". Thus, the actual pill removal is assumed to be a precursor of administration of the pill by the patient consistent with the prescribed regimen. The relevant marker designating the time, dosage, and the type of medication is generated within a various diagnostic tables, and trend curves representing different physiologic parameters.

Further, IMDs 10, 10' and 10" chronically monitor the physiological parameters of the patient and may alert the patient in cases, for example, when the drug does not influence a trend curve, causes the trends curve to oscillate, patient is not following the prescribed regimen or patient stops taking the medication altogether. Subsequently, IMDs 10, 10' and 10" could alert the physician or clinician to confer with the patient. This may be done via programmer 20 up-linking to data center 62. The Physician at station 120 will be able to access the patient data from data center 62. As shown in FIG. 5, Pill dispenser 20' is in data communication with data center 62. Thus the status of pill dispenser 20' is registered in either device or patient databases for the clinician to investigate.

Pill dispenser 20' is generally structured with a plurality of metallic layers such as 102 and 104, preferably aluminum and plastic layers. Thus, in one embodiment pill dispenser 20' acts as a capacitor cell. Piezoelectric film 106 is similar to commercially available Kynar or equivalent, sandwiched between the two layers. Accordingly, whenever the patient manipulates pill dispenser 20' to break container 100 and remove a pill, a voltage will be produced within the piezoelectric film. This voltage may be used as a signal to the IMDs indicating the removal of a pill. Specifically, the signal being different from ECG, EMG, EMI or any other body generated signal, is suited to be used as a signal from pill dispenser 20' to IMDs 10. 10' and 10". IMDs 10, 10' and 10" may be programmed to identify this signal as an indication that the seal has been opened and that a pill has been ingested by the patient. In the alternate, pill dispenser 20' may be used as a capacitor in a resonant circuit. Under this approach, when the patient presses the pill dispenser 20' the impedance is changed due to the skin-metal impedance change and consequently the resonance circuit may be closed by the patient's hands. Accordingly, IMDs 10, 10' and 10" are able to monitor dose data and related clinical parameters by communicating with pill dispenser 20'. The measurements performed by IMDs 10, 10' and 10" are specific to the type of preprogrammed criteria and determinants thereof. However, in the context of the present invention, IMDs 10, 10' and 10" could be programmed to monitor a given pill dispenser 20' on a chronic basis. This will provide a stream of data that will indicate whether the patient has been following a prescribed dose and regimen. Further, IMDs 10, 10' and 10" may be programmed to monitor the efficacy of the drug by monitoring the physiological effects of the drug on the patient. Accordingly, a direct, real time assessment and interpretation of clinical status is obtained under the communication scheme advanced by the present invention.

Referring to programmer 20 in more detail, when a physician or an operator needs to interact with programmer 20, a keyboard coupled to Processor 80 is optionally employed. However the primary communication mode may be through graphics display screen of the well-known "touch sensitive" type controlled by graphics circuit. A user of programmer 20 may interact therewith through the use of a stylus, also coupled to a graphics circuit, which is used to point to various locations on a screen/display to display menu choices for selection by the user or an alphanumeric keyboard for entering text or numbers and other symbols as shown in the above-incorporated '362 patent. Various touch-screen assemblies are known and commercially available. The display and or the keyboard of programmer 20, preferably include means for entering command signals from the operator to initiate transmissions of downlink telemetry from IMDs and to initiate and control telemetry sessions once a telemetry link with one or more IMDs has been established. The graphics display /screen is also used to display patient related data and menu choices and data entry fields used in entering the data in accordance with the present invention as described below. The graphics display/screen also displays a variety of screens of telemetered out data or real-time data. Programmer 20 is also provided with a strip chart printer or the like coupled to interface controller module so that a hard copy of a patient's ECG, EGM, marker channel or similar graphics display can be generated. Further, Programmer 20's history relating to instrumentation and software status may be printed from the printer. Similarly, once an uplink is established between programmer 20 and any one of IMDs 10, 10' and 10", various patient history data and IMD performance data may be printed out. The IMDs contemplated by the present invention include a cardiac pacemaker, a defibrillator, a pacer-defibrillator, implantable monitor (Reveal), cardiac assist device, and similar implantable devices for cardiac rhythm and therapy. Further the IMD units contemplated by the present invention include electrical stimulators such as, but not limited to, a drug delivery system, a neural stimulator, a neural implant, a nerve or muscle stimulator or any other implant designed to provide physiologic assistance or clinical therapy. Any implantable medical device implanted within the body and capable of remote communication may be utilized within the scope of the present invention.

Data center 62 represents a high speed computer network system having wireless bi-directional data, voice and video communications with programmer 20 and/or pill dispenser 20' via wireless communications link 136. Generally data center 62 is preferably located in a central location and is preferably equipped with high-speed web-based computer networks. Preferably, data center 24 is manned 24-hours by operators and clinical personnel who are trained to provide a web-based remote service to programmer 20 and/or pill dispenser 20'. In accordance with the present invention, data center may be located in a corporate headquarters or manufacturing plant of the company that manufactures programmer 20. The wireless data communications link/connections can be one of a variety of links or interfaces, such as a local area network (LAN), an internet connection, a telephone line connection, a satellite connection, a global positioning system (GPS) connection, a cellular connection, a laser wave generator system, any combination thereof, or equivalent data communications links.

As stated hereinabove, bi-directional wireless communications D, E and F act as a direct conduit for information exchange between remote data center 62 and programmer 20, pill dispenser 20' and physician center 120, respectively. Further, bi-directional wireless communications A and B provide an indirect link between remote data center 62 and IMDs 10, 10' and 10" via programmer 20 and pill dispenser 20'. In the context of this disclosure the word "data" when used in conjunction with bi-directional wireless communications also refers to sound, video and information transfer between the various centers.

Generally, in the context of the invention, all programmers located proximate to IMDs or patients with IMDs and distributed globally are connected to an expert data center to share software upgrades and access archived data. The programmer functions as an interface between the remotely located expert data center and the IMDs. Further, procedural functions such as monitoring the performance of the IMDs, upgrading software in the IMDs, upkeep and maintenance of the IMDs and related functions are implemented via the programmer. The preferably telemetric and yet local interaction between the programmer and the IMDs needs to be managed by a qualified operator. In order to facilitate the just-in-time patient care at the location of the patient, the invention provides pill dispenser 20' that is preferably wirelessly linked to data center 62. This scheme enables the dissemination of drug related clinical information worldwide while maintaining a high standard of patient care at reduced costs.

Figure 6:
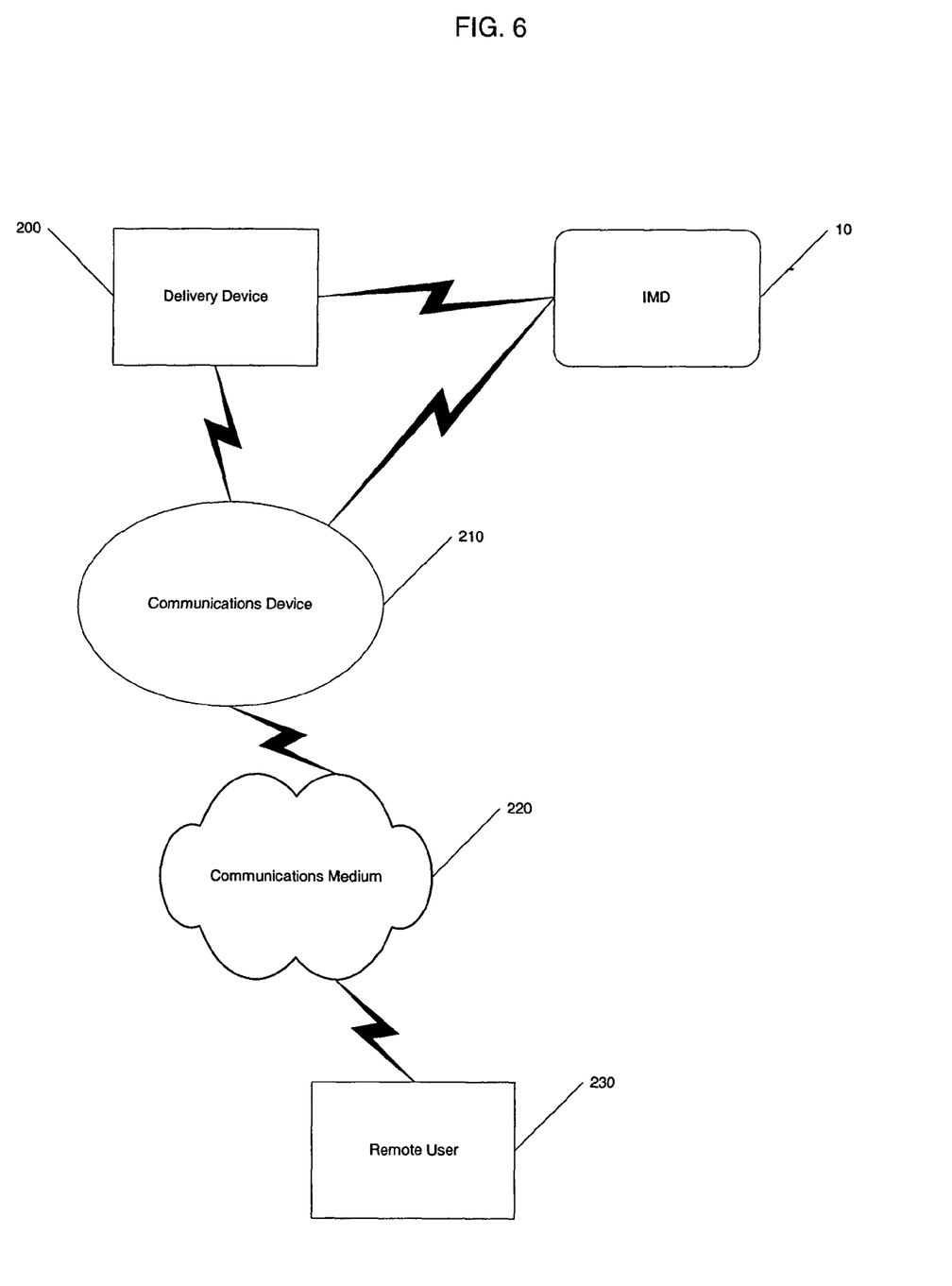
FIG. 6 is a block diagram illustrating an overview of the communication between an IMD, a delivery device, a communications device and a remote user.

As described herein with respect to certain embodiments, there is an interaction between an IMD 10 and a pill dispenser 20'. For example, in one embodiment, the pill dispenser 20' signals the IMD 10 when a dose is about to be taken. Thus, the IMD 10 can track the patient's drug intake and react accordingly. FIG. 6 illustrates, in a general block diagram, a higher level overview of the present invention.

Referring to FIG. 6, IMD 10 is illustrated and would be implanted within a patient. A drug delivery device 200 is utilized to contain and/or deploy some drug therapy for that patient. Drug delivery device 200 is in telemetered communication with IMD 10, either directly or through a communications device 210. For example, in one embodiment delivery device 200 is pill dispenser 20' and communications device 210 is programmer 20. IMD 10, delivery device 200, and/or communications device 210 may be in communication with a remote user 230 through a communications medium 220. For example, in one embodiment communications medium 220 is the Internet and remote user 230 is the expert data center 62.

The interaction between delivery device 200 and IMD 10 can take many forms. As previously described, delivery device 200 indicates in one embodiment when a dose is taken. In addition, the IMD 10 senses many parameters within the patient and based on these parameters further interacts with the delivery device 200. Such parameters include, but are not limited to: heart rate/rhythm, blood pressure, fluid pressure, flow rates/velocity, electrical activity (cardiac, neural, or other), temperature, activity levels, orientation, breathing, minute ventilation, glucose levels, drug levels, complex physiology (e.g., organ acceptance), or virtually any measurable or sensible parameter. With such sensing capabilities, the IMD can utilize relatively sophisticated processing capabilities to respond to the sensed criteria. Such processing occurs within the IMD 10 itself, within the communications device 210 (e.g., programmer 20) or at a remote site (e.g., data center 62).

Based on what is sensed by IMD 10, various appropriate actions can be taken. For example, certain sensed parameters may indicate that the delivered drug dosage should be increased, decreased, stopped, or a new drug should be used. This information can be transmitted to the drug delivery device 200 and such adjustments are implemented. Alternatively, the patient is notified of the changes. Such patient alerts are delivered by the IMD (voice, vibration, audible tones, etc.), by similar means on the delivery device 200, or through other communications mechanisms. For example, remote user 230 could call or email a patient with information. Such communications may be made by a human or automatically generated.

Thus, the IMD senses conditions and effectuates drug delivery changes or modifications to the IMD therapy based on a lack of drug delivery or ineffectiveness of the drug delivery. Conversely, the drug delivery device 200 senses conditions and communicates with IMD 10 to effectuate changes in the therapy delivered by the IMD 10. As previously discussed, drug delivery device 10 indicates when a dose is missed or a prescription has run out.

Drug delivery device 200 can take many forms and facilitate various sensing and communication options. As previously discussed, in one embodiment drug delivery device 200 is a pill dispenser having a transmitter that signals when a pill is removed from a package, thus indicating that the pill is about to be taken. Drug delivery device 200 could be a medicine container containing pills, powders, liquids or other drug forms. The container includes means for monitoring the amount taken and the amount remaining. The container could include a locking mechanism to prevent access. In a hospital or clinical setting, drug delivery device 200 could be a medicine cabinet/cart having restricted access. Furthermore, the container could include automatic dosing functions to deliver a specific dose to the patient at a predetermined interval. For example, the container could dispense two pills every two hours. Thus, the rate and access are controllable and are adjustable based on communications with the IMD 10 or remote user 230.

In other embodiments, drug delivery device 200 is a transcutaneous delivery mechanism, a subcutaneous delivery mechanism, an oral drug dispenser, an IV unit, a transdermal patch, a syringe, an inhaler, or virtually any form of drug dispenser or delivery mechanism. In each embodiment, some aspect of the delivered dosage is controllable based on input from the IMD 10 or the remote user 230. Such control is automatic (e.g., automatically adjusting the volume of dispersal for an inhaler) or is in the form of instructions to the patient (e.g., take two doses of an oral medication rather than one).

As the drug delivery mechanism 200 takes many diverse forms, communication between the delivery mechanism 200 and IMD 10 is likewise affected through various mechanisms. In some embodiments, the drug delivery mechanism includes communications capabilities to facilitate direct communication with the IMD 10. In other embodiments, such communication occurs through an intermediary device, such as communication device 210. As previously discussed, programmer 20 may serve as communication device 210. Alternatively, other devices may interface between the drug dispenser 200 and IMD 10. For example, electronic watches, cell phones, pagers, PDA's, laptop/desktop computers, patient activators, televisions, a dedicated remote monitor, a voice synthesizer, or visual indicia (e.g., LEDs on a pill box) can be used in this capacity. Again, the action taken is automatic (e.g., a change in dosage) or is instructional (e.g., alerting the patient to self-adjust a dosage).

In one embodiment, a patient activator is provided that is in communication with the IMD 10, either directly or through the delivery device 200. The patient activator is used to signal the IMD to record data because the patient has undergone a noteworthy medical event, to trigger therapy, or to otherwise interact with the IMD 10. For example, the IMD could be a neurostimulator used to alleviate pain. At the onset of pain, the patient triggers the IMD 10 to stimulate a nerve and relieve the pain. In the context of the present invention, the patient activator is also used to signal that the patient has taken a prescribed drug, thus serving as the communications device 210 to interface between the drug delivery device 200 and the IMD 10.

The present invention, in one embodiment, also provides an automatic prescription refill function. As the patient's supply within the delivery device 200 nears depletion, a communication is sent to the remote user 230, in this case a pharmacy, to automatically reorder the prescription. The drug delivery device 200 includes sufficient identification information to allow the pharmacy to process the request. In addition, as the IMD 10 senses parameters and a determination is made to change drug therapies, the new prescription or dosing information is automatically processed to the pharmacy. Similarly, in one embodiment, the remote user 230 is a monitoring physician and any drug changes are suggested and/or approved by that physician. Alternatively, the IMD 10 communicates with the pharmacy. The IMD 10 includes certain identifying information relating to the patient, thus a level of secure identification is provided for facilitating the prescription refill.

In another embodiment, the remote user 230 is an emergency room. The IMD 10 and/or delivery device 200 provide critical information to the emergency room to indicate the nature of a problem. This can trigger the dispatch of emergency services (e.g., an ambulance) and/or will provide important diagnostic and treatment information. For example, if a critical drug dosage is missed over an extended period of time, this may indicate a serious adverse condition. Alternatively, the delivery device 200 indicates that a patient took an inappropriate drug that has serious consequence requiring medical attention. Of course, in cases were the consequences are less sever, a communication could simply be sent to the patient advising them of the error.

Various medical conditions require or optimally utilize combination therapies for treatment. That is, an IMD 10 delivers one therapy while a drug regime provides a complimentary therapy. Such situations are well adapted for use with the present invention. For example, patients having long QT syndrome often have an implantable pacemaker and take a beta blocker. With the present invention, if a dosage of the beta blocker is missed, the IMD 10 is alerted and increases the pacing rate to prevent the elongation of the QT interval. In patients having heart failure, the IMD 10 monitors various hemodynamic conditions such as the right ventricular filling pressure. Thus, as the pressure changes, IMD 10 can direct delivery device 200 to increase or decrease the delivery of a diuretic or vasodilator. As another example, patients having ischemic heart disease or coronary artery disease may have an IMD 10. If the IMD 10 detects ischemia, the IMD 10 can alert the patient or direct the drug delivery device 200 to provide an appropriate blood thinner such as aspirin, nitroglycerin, or a vasodilator. Many other effects of medical conditions can be monitored and the therapy controlled. Furthermore, the IMD 10 can monitor conditions beyond those related to the therapy delivered. For example, a cardiac related IMD could also include sensors to monitor insulin levels and direct delivery device 200 accordingly. Likewise, delivery device 200 may be an IMD itself, for example, a drug pump. Thus, the sensing effects may be incorporated into the same unit or a separate IMD may communicate with the implanted drug delivery device.

Figure 7:
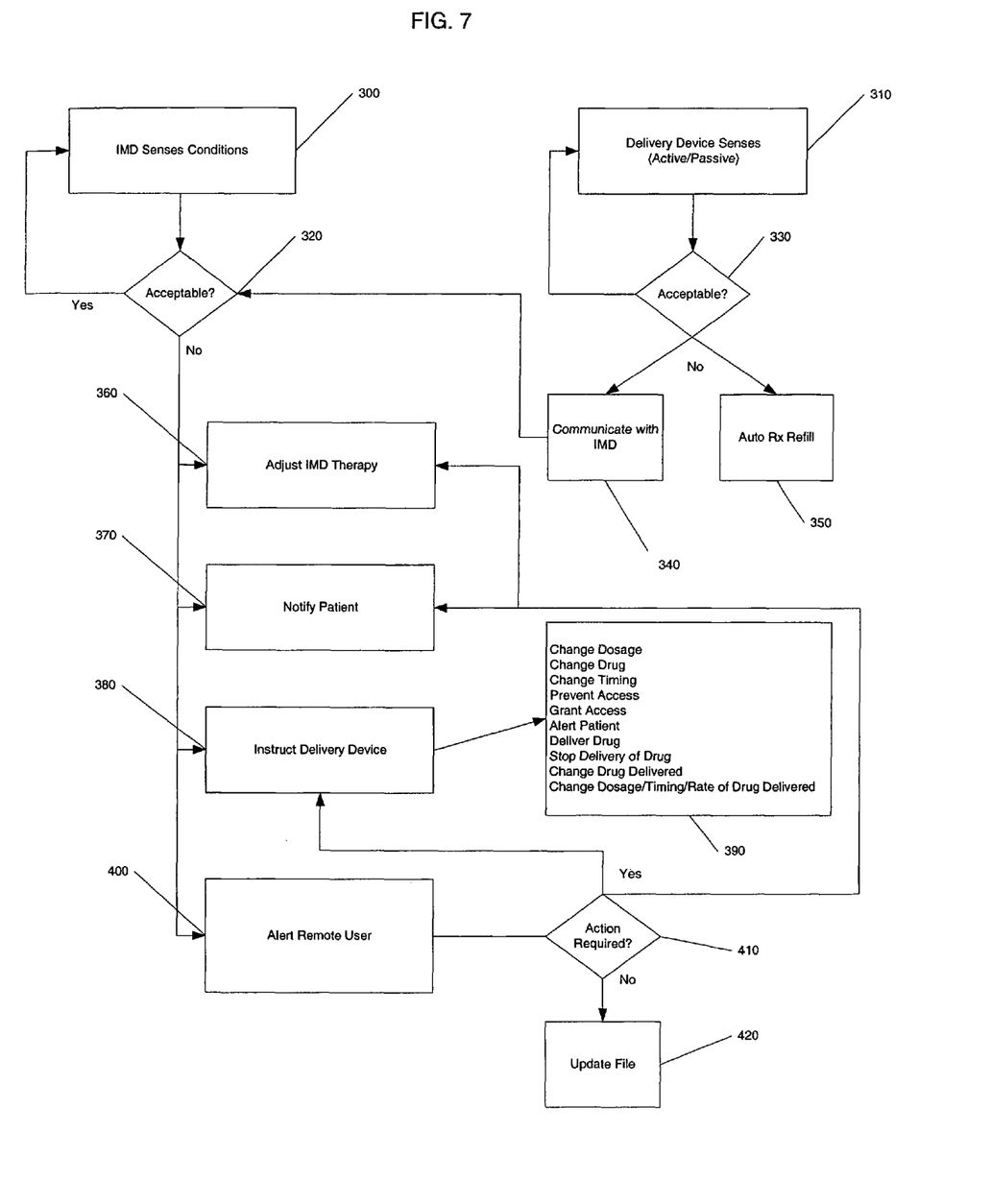
FIG. 7 is a flow chart illustrating the process of interaction between an IMD and a Delivery Device.

FIG. 7 is a flowchart illustrating one embodiment of the present invention. The IMD 10 within the patient senses (300) certain conditions within the patient. The IMD (alone or in conjunction with external processing, e.g., a programmer 20) determines if the sensed parameters are acceptable (320). Concurrently, the drug delivery device 200 is sensing (310) its parameters, if so enabled. As used in this context, the sensing of the delivery device 200 includes various possible parameters. For example, sensing would include the delivery or the failure to deliver/take a dosage. In addition, sensing could include the sensing of physiological conditions. For example, if the delivery device is a transdermal patch, the patch could detect the presence of the drug in the tissue that indicates successful delivery in addition to deployment. If the delivery device is an IV unit, sensing would include, for example, the remaining amount of the drug or medicament being administered, the operation of the pump, the rate of delivery, the connection with the patient, and the successful delivery to the patient The delivery device determines whether the sensed parameters are acceptable (330). This can be done entirely within the delivery device if so enabled, or the data may be passed to the IMD or the communications device (e.g., a programmer) and the processing occurs there. In either event, if an unacceptable parameter is sensed (e.g., a missed dose), the information is passed to the IMD (340). Alternatively, if the unacceptable parameter is that the drug supply is low, the delivery device communicates (350) with a pharmacy to automatically refill the prescription. In a hospital or similar setting, such communication could be directed to a nursing station to request resupply.

Thus, as indicated at 320, unacceptable parameters could be identified from the IMD or from the drug deliver device (directly or through communication device 210). Once an unacceptable parameter is identified, the IMD has four basic options. First, the therapy delivered by the IMD may be modified (360). As explained above, if information is received indicating a missed dosage, a pacing therapy could be altered, as one example. The second option is to notify (370) the patient. This could occur internally from the IMD. For example, the IMD would vibrate, generate a tone, or generate a voice prompt. The IMD could transmit to the drug delivery device to generate a patient alert. For example, if the drug delivery device is a pill container, the container could include audible warnings/indicators or visual indicators such as lighting elements or text displays. This serves to help remind the patient to take a dosage. Likewise, the IMD could generate the same type of patient reminders through the communication device 210. Finally, through any of these mechanisms, an automated electronic alert could be initiated, such as an email, page, telephone call with prerecorded message, or the like.

The third option for the IMD is to instruct (380) the delivery device to take some action. The possible actions vary and many are illustrated above. By way of example, several such options (390) are presented in the flowchart. These include changing a dosage; changing the drug itself; changing the timing of dosages; preventing access (e.g., locking the container); granting access (e.g., unlocking the container); alerting the patient through the delivery device; stopping delivery of the drug when such delivery is automated (e.g., IV, patch, etc.); automatically changing the drug delivered when such delivery is automated and another drug is available (e.g., a drug pump, IV); and changing the dosage, timing or rate of drug delivery when such delivery is automated. These options are not meant to be exhaustive, merely illustrative.

The fourth option for the IMD is to alert the remote user (400). For example, if a combination therapy such as pacing and drug delivery is meant to control arrhythmia and is proving ineffective, an alert may be sent to the monitoring physician with or without a recommendation to alter the drug therapy. Of course, once so alerted the remote user (either human or automated) evaluates the situation (410) to determine if action is required. If it is not, then the patient file is merely updated (420). If action is required, the remote user can initiate any of the three options discussed above. That is, alerting the patient, altering the IMD therapy, or adjusting the drug therapy via the patient or via the delivery device.

It should be appreciated that the four options presented are not mutually exclusive and that there is overlap among the options. That is, the IMD, in some contexts may perform more than one and possibly all of the options.

Although specific embodiments of the invention have been set forth herein in some detail, it is understood that this has been done for the purposes of illustration only and is not to be taken as a limitation on the scope of the invention as defined in the appended claims. It is to be understood that various alterations, substitutions, and modifications may be made to the embodiment described herein without departing from the spirit and scope of the appended claims.

The invention claimed is:

1. An interactive remote drug dose and physiologic response monitoring system in a patient under a prescriptive regimen to take a drug comprising:
    a drug delivery device; and
    an implantable medical device (IMD) in wireless communication with the drug delivery device, the IMD having means for receiving, from the drug delivery device, a communication indicating administration of a drug by the drug delivery device in compliance with a prescriptive regimen,
    wherein the IMD is configured to modify at least one therapy delivered by the IMD based on the communication indicating administration of the drug by the drug delivery device.

2. The system of claim 1, wherein the delivery device is chosen from one of the following: a pill box, a transdermal patch, a IV, an inhaler, an oral medicament dispenser, a subcutaneous implant, or a drug pump, or a transcutaneous application.

3. The system of claim 1, wherein the IMD checks drug interaction in the patient subsequent to the administration of the drug.

4. The system of claim 1, wherein the IMD determines at least one parameter selected from the group consisting of:
    drug intake by the patient in compliance with the prescriptive regimen;
    a dosage of the drug administered by the drug delivery device; and
    an impact of administration of the drug on the IMD.

5. The system of claim 1, further comprising:
    means for logging monitored parameters of the drug delivery device.

6. The system of claim 1, wherein the drug delivery device includes a pill dispenser.

7. The system of claim 6, wherein the IMD determines at least one parameter of the drug delivery device selected from the group consisting of:
    a number of pills in the pill dispenser;
    a number of pills taken by the patient via the pill dispenser; and
    a dosage of the drug taken by the patient from the pill dispenser.

8. The system of claim 1, wherein the IMD is one of a neurostimulator or a cardiac stimulator.

9. A drug delivery monitoring system comprising:
    means for monitoring parameters of a drug delivery device;
    means for communicating the monitored parameters with an implantable medical device (IMD);
    means for processing the monitored parameters; and
    means for controlling a therapy delivered by the IMD based upon the monitored parameters of the drug delivery device.

10. The system of claim 9, further comprising:
    means for sensing physiological parameters through the IMD;
    means for processing the sensed physiological parameters relative to a drug delivered by the drug delivery device; and
    means for controlling the drug delivery device in response to the processing of the sensed physiological parameters.

11. The system of claim 9, wherein the means for communicating monitored parameters with an IMD is included in the drug delivery device.

12. The system of claim 9, wherein the means for communicating communicates directly with the IMD.

13. The system of claim 9, further comprising:
an intermediary device, wherein the means for communicating communicates the monitored parameters with the IMD via the intermediary device.

14. The system of claim 13, wherein the means for processing the monitored parameters is included in the intermediary device.

15. The system of claim 9, wherein the means for processing the monitored parameters is included in the IMD.

16. The system of claim 9, wherein the means for processing the monitored parameters is included in the means for communicating.

17. The system of claim 9, wherein the means for processing the monitored parameters is remote from the IMD.

18. An implantable medical device comprising:
a controller for controlling cardiac therapy parameters; and
one or more electrodes for delivering electrical stimulation to cardiac tissue and monitoring physiologic parameters of the tissue;
wherein the controller receives the parameters from the one or more electrodes and information from a drug delivery device, the information identifying whether an expected drug therapy is delivered, wherein the controller varies the cardiac therapy delivery through the one or more electrodes based upon the parameters and the information.

19. The device of claim 18, wherein the delivery device includes at least one drug delivery device selected from the group consisting of:
a pill dispenser;
a transdermal patch;
an IV;
an inhaler;
an oral medicament dispenser;
a subcutaneous implant;
a drug pump; and
a transcutaneous application.

20. The device of claim 18, wherein the information identifying whether an expected drug therapy is delivered includes information selected from the group consisting of:
information identifying drug intake by a patient;
information identifying whether the expected drug therapy is delivered by the drug delivery device; and
information identifying dosage of a drug delivered by the drug delivery device.

21. The device of claim 18, wherein the expected drug therapy includes delivery of a beta blocker, wherein if the information identifying whether an expected drug therapy is delivered indicates that the therapy was not delivered, the controller adjusts a pacing rate of cardiac therapy delivered through the one or more electrodes.

22. The device of claim 18, wherein the controller varies the cardiac therapy delivery by modifying delivery of electrical stimulation to cardiac tissue.

* * * * *